(12) United States Patent
Lerner et al.

(10) Patent No.: US 7,523,751 B2
(45) Date of Patent: Apr. 28, 2009

(54) DEVICE AND METHOD FOR PROVIDING A CONTROLLED MIXTURE OF GAS AND VAPOR TO A PATIENT

(75) Inventors: Israel Lerner, Kibbutz Netser-Sereni (IL); Zeev Rosner, Kibbutz Netser-Sereni (IL)

(73) Assignee: Ultra Rhino Therm Ltd., Kibbutz Netser-Sereni (IL)

( * ) Notice: Subject to any disclaimer, the term of this patent is extended or adjusted under 35 U.S.C. 154(b) by 232 days.

(21) Appl. No.: 11/381,694

(22) Filed: May 4, 2006

(65) Prior Publication Data

US 2007/0256686 A1 Nov. 8, 2007

(51) Int. Cl.
*A61M 16/00* (2006.01)
(52) U.S. Cl. ............ 128/203.26; 128/203.16; 261/141; 261/142
(58) Field of Classification Search ......... 128/203.26, 128/203.27, 200.14, 203.12, 203.16, 203.17; 261/141, 142
See application file for complete search history.

(56) References Cited

U.S. PATENT DOCUMENTS

| | | | | |
|---|---|---|---|---|
| 4,722,334 A | * | 2/1988 | Blackmer et al. | 128/203.16 |
| 5,243,973 A | * | 9/1993 | Falb et al. | 128/203.27 |
| 5,361,322 A | * | 11/1994 | Glucksman | 392/405 |
| 5,832,917 A | * | 11/1998 | Sarela et al. | 128/203.12 |
| 6,761,164 B2 | * | 7/2004 | Amirpour et al. | 128/203.26 |
| 6,988,497 B2 | * | 1/2006 | Levine | 128/203.27 |

* cited by examiner

*Primary Examiner*—Steven O Douglas
(74) *Attorney, Agent, or Firm*—Pearl Cohen Zedek Latzer LLP

(57) ABSTRACT

A method including: providing a device that includes multiple tilted heating elements, and a housing that includes a fluid reservoir inlet that is adapted to receive an inverted fluid reservoir, a gas inlet that is adapted to receive pressurized gas from a gas pipe, a gas-vapor outlet; and activating the device to provide a controller mixture of gas and fluid. A device including: multiple tilted heating elements, and a housing that includes a fluid reservoir inlet that is adapted to receive an inverted fluid reservoir, a gas inlet that is adapted to receive pressurized gas from a gas pipe, a gas-vapor outlet; wherein the multiple tilted elements are placed at least partially within fluid within the housing and are adapted to heat the fluid such as to generate vapors; wherein the device is adapted to output, via the gas vapor outlet a mixture of gas and vapor.

10 Claims, 3 Drawing Sheets providing a device that includes multiple tilted heating elements, and a housing that includes a fluid reservoir inlet that is adapted to receive an inverted fluid reservoir, a gas inlet that is adapted to receive pressurized gas from a gas pipe, a gas vapor outlet and a optionally a gas directing barrier that is positioned between the gas inlet and the gas stream outlet such as to direct gas to flow towards the gas-stream outlet.

220 setting the temperature of the mixture of gas and fluid by adjusting the device.

230 activating the device to provide a controller mixture of gaseous medium and vapor.

DEVICE AND METHOD FOR PROVIDING A CONTROLLED MIXTURE OF GAS AND VAPOR TO A PATIENT

FIELD OF THE INVENTION

The present invention relates to a device and a method for providing a controlled mixture of gas and vapor to a patient and especially for treating rhinitis.

BACKGROUND OF THE INVENTION

It has been known for some time that the application of a hot medium (usually air) to the nose of a patient suffering from rhinitis results in a sensible relief thereof, due both to the opening of the respiratory tracks and the sterilization thereof. However, in order to obtain a useful action of the hot medium and to avoid harmful effects or an uncomfortable feeling during treatment, the hot medium employed must fulfill certain requirements. Throughout this specification reference will be made to air as the hot medium, for the sake of simplicity, it being understood that any other suitable gaseous medium may be employed instead of air, with the corresponding operational changes.

As stated, the hot air must fulfill certain conditions. The temperature of the air, for instance, should not exceed 47° C. in order to avoid damage to the mucous membrane of the patient's nose. Further, the humidity of the air must be as high as possible in order to avoid discomfort and a feeling of dryness in the patient. Maintaining these conditions usually required using relatively costly control mechanisms. In addition, many prior devices required using distilled water, which is more expensive than non-distilled water.

The following patents and patent applications, all being incorporated herein by reference, describe various devices and methods for providing a mixture of air and vapor: U.S. Pat. No. 4,805,614 of Lerner, U.S. patent application publication 2004231668 of Kates, U.S. Pat. No. 5,483,953 of Cooper, Japanese patent application JP2000051355, Japanese patent application JP1995000036455 of Terada et al., Japanese patent application JP1991000220036 of Watari et al., FR2595251 of Lwoff et al., and PCT patent application publication serial number WO03059425 of Jiang et al.

There is a growing need to provide inexpensive and efficient devices and method for providing a controlled mixture of gas and vapor to a patient.

SUMMARY OF THE INVENTION

According to an embodiment of the invention a device is provided. The device includes multiple tilted heating elements located within a housing; wherein the housing includes: (i) a fluid reservoir inlet that is adapted to receive a fluid reservoir, (ii) a gas inlet that is adapted to receive pressurized gas, and (iii) a gas-vapor outlet. The housing defines a hollow space in which gas and vapor mix heated and fluid that flows from the fluid reservoir.

Conveniently, the temperature of the mixture of gas and vapor can be set to a certain level by using a predefined fluid and determining the height of the fluid reservoir. For example, the temperature of the mixture of gas and vapor may be set by setting the tilt angle between the multiple heating elements (or equivalently—setting the angle between the multiple heating elements) and/or determining the distance between the multiple heating elements.

According to an embodiment of the invention the bottom of the housing includes a sloped portion, and a lower portion (such as a U-shaped portion) that starts at the lower end of the sloped section. Fluid from the inverted fluid reservoir flows along the sloped portion towards the U-shaped portion. The lower portions of the tilted heating elements are positioned within the space defined by the U-shaped portion.

Conveniently, the level of the fluid within the housing is determined by the position of the outlet of the inverted fluid reservoir. According to an embodiment of the invention, in order to maintain substantially the same temperature during different activations of the device, there is a need to use substantially the same fluid and to position the fluid reservoir at substantially the same height. According to yet another embodiment of the invention an additional fluid can be added to the gas and vapor mixture, conveniently by using a mixing system.

BRIEF DESCRIPTION OF THE DRAWINGS

The present invention will be understood and appreciated more fully from the following detailed description taken in conjunction with the drawings in which:

FIG. 3 is a flow chart of a method for providing a controlled mixture of gaseous medium and fluid, according to an embodiment of the invention.

DETAILED DESCRIPTION

According to various embodiments of the invention a mixture of gas and vapor is provided to a client. The temperature and the humidity of the mixture can be maintained by using substantially the same fluid and by supplying the same amount of fluid to the device. The device heats a fluid such as water to provide vapor by using tilted heating elements. When the fluid is boiled, bubbles are formed. Bubbles are formed on the surface of the fluid and below the surface of the fluid. Bubbles that are formed on the surface of the fluid increase the effective contact area of the heating elements thus increase the amount of vapors that are produced by the fluid heating process. On the other hand, bubbles that are formed within the fluid reduce the heat conductivity of the fluid and eventually reduce the amount of vapor that is generated by the fluid heating process.

In order to maintain a steady amount of bubbles, tilted heating elements are used. Their tilt reduces the amount of bubbles that are formed over the surface while increasing the amount of bubbles formed within the fluid. The inventors used a device in which the angle ($\alpha$) between a first and a second heating element (such as an electrode) ranged between one degree and thirty degrees.

Figure 1:
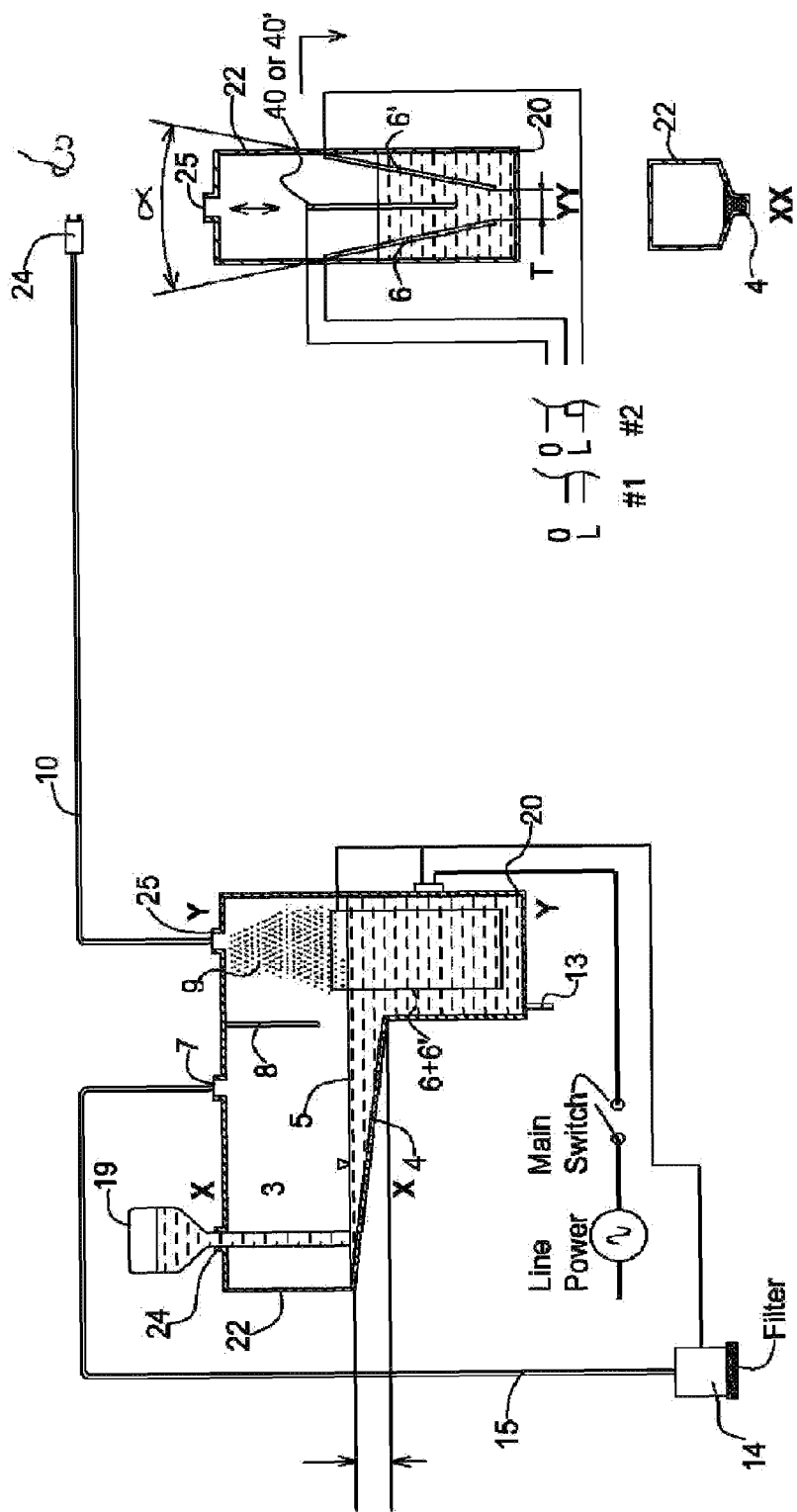
FIG. 1 illustrates three cross sections of a device configured according to an embodiment of the invention.

FIG. 1 illustrates three cross sections of device 1 according to an embodiment of the invention. The first cross section is taken along an imaginary longitudinal axis. The other two cross sections were taken along two latitudinal axes X-X and Y-Y.

The inventors used a housing 22 that included a sloped portion that was oriented (in relation to the horizon) at an angle ($\beta$) that ranged between zero and ten degrees.

According to an embodiment of the invention the device includes a housing 22 that is adapted to receive an inverted fluid reservoir 19. The inverted fluid reservoir 19 has a fluid outlet. The level (denoted 5) of the fluid within the housing 22 is determined by the location (height) of the fluid outlet of the inverted reservoir 19.

In order to reduce unnecessary heating of the fluid 2 within the inverted fluid reservoir 19, by the heating elements 6 and 6', the bottom of the housing 22 includes a sloped portion 4, such that the volume of fluid that contacts the fluid outlet of the inverted fluid reservoir 19 is relatively small. In addition, vapor and heat that exit the fluid are forced to exit housing 22 by the gas stream that flows through housing 22.

Device 1 includes multiple tilted heating elements, such as tilted electrodes 6 and 6' that are located within housing 22. The housing 22 includes fluid reservoir inlet 24 that is adapted to receive an inverted fluid reservoir 19, gas inlet 7 that is adapted to receive pressurized gas from gas pipe 15, gas-vapor outlet 25 and gas directing barrier 8 that is positioned between the gas inlet 7 and the gas-vapor outlet 25 such as to direct gas to flow towards the gas-vapor outlet 25. The gas inlet 7 is vertical and it directs gas downwards, while the gas-vapor outlet 25 is also vertical. The gas directing barrier 8 is a vertical plate that forces gas to pass beneath it and then to propagate upwards, towards the gas-vapor outlet.

The housing 22 is illustrated as having multiple vertical inlets and outlets on its horizontal upper part, but other configuration can be used.

Conveniently, the temperature of the mixture of gas and vapor can be set to a certain level by using predefined fluid and determining the height of the fluid reservoir. The height of the fluid is defined by the height of the inverted fluid reservoir 19. The inventors used an inverted fluid reservoir that has a certain projection that is shaped so as to contact the fluid reservoir inlet 24 and maintain the inverted fluid reservoir at a certain height.

The temperature of the mixture of gas and vapor is set by setting the tilt angle between the multiple heating elements (or equivalently—setting the angle between the multiple heating elements) and determining the distance between the multiple heating elements.

According to one embodiment the distance (T) between the heating elements is fixed but different devices can be characterized by setting (tilt angle, distance) of the heating elements. According to yet another embodiment of the invention the heating elements can be positioned in different positioned, thus allowing an alteration of the temperature of the heated fluid.

Optionally, another element such as element 40 can be placed into the fluid. If that element is made of a conductive material it can increase the heating of the fluid. If is made of isolating material it can decrease the heating. It is further notes that vertically shifting this element can increase or decrease the heating.

The bottom of the housing includes a sloped duct portion 4 and a lower (such as U-shaped) portion 20 that starts at the lower end of the sloped portion 4. Fluid from the inverted fluid reservoir 19 flow along the sloped portion 4 towards the U-shaped portion 20. The lower portions of the tilted heating elements 6 and 6' are positioned within the space defined by the U-shaped portion 20.

Conveniently, the level (denoted 5) of the fluid within the housing 22 is determined by the position of the fluid outlet of the inverted fluid reservoir 19.

According to an embodiment of the invention, in order to maintain substantially the same temperature during different activations of the device there is a need to use substantially the same fluid and to position the fluid reservoir at substantially the same height. A fluid having a certain conductivity level can be replaced by another fluid having substantially the same conductivity level.

Gas is forced into the housing 22 by a compressor 14 that can include a motor and a filter that enables filtered gas to flow towards gas pipe 15. The gas then flows through gas inlet 7 of housing 22 and into a hollow space 3, over gas directing barrier 8 and then exits housing 22, after being mixed with vapor, through gas-vapor outlet 25, output pipe 10 and nozzle 24.

The U-shaped portion 20 is connected to a drainage tap 13.

A thermal switch 42 can stop the flow of current through the heating elements to prevent overheating of the fluid.

The device 1 according to the invention typically operates as follows. Voltage is applied to tilted heating elements 6 and 6' that in turn heat fluid such as to generate vapor 9. In addition, gas flows from compressor 14, via gas pipe 15, via gas inlet 7 to space 3. Accordingly both gas and vapor are provided to space 3 is mixed with humid 9 and is forced to exit housing 22 via gas-vapor outlet 25. The mixture of gas and vapor is formed above heating elements 6 and 6'. The mixture flows through gas-vapor outlet 25, pipe 10 and nozzle 24 towards a patient.

Because of the steady-state conditions at which the device is caused to operate, it is enough to provide a set point for the heat input to the vapor generating device once, and then the quality of the out-flowing humid air (temperature and humidity) will remain stable as long as the water reservoir is full. Therefore, no complex feedback control circuits are required for the satisfactory operation of the device.

Figure 2:
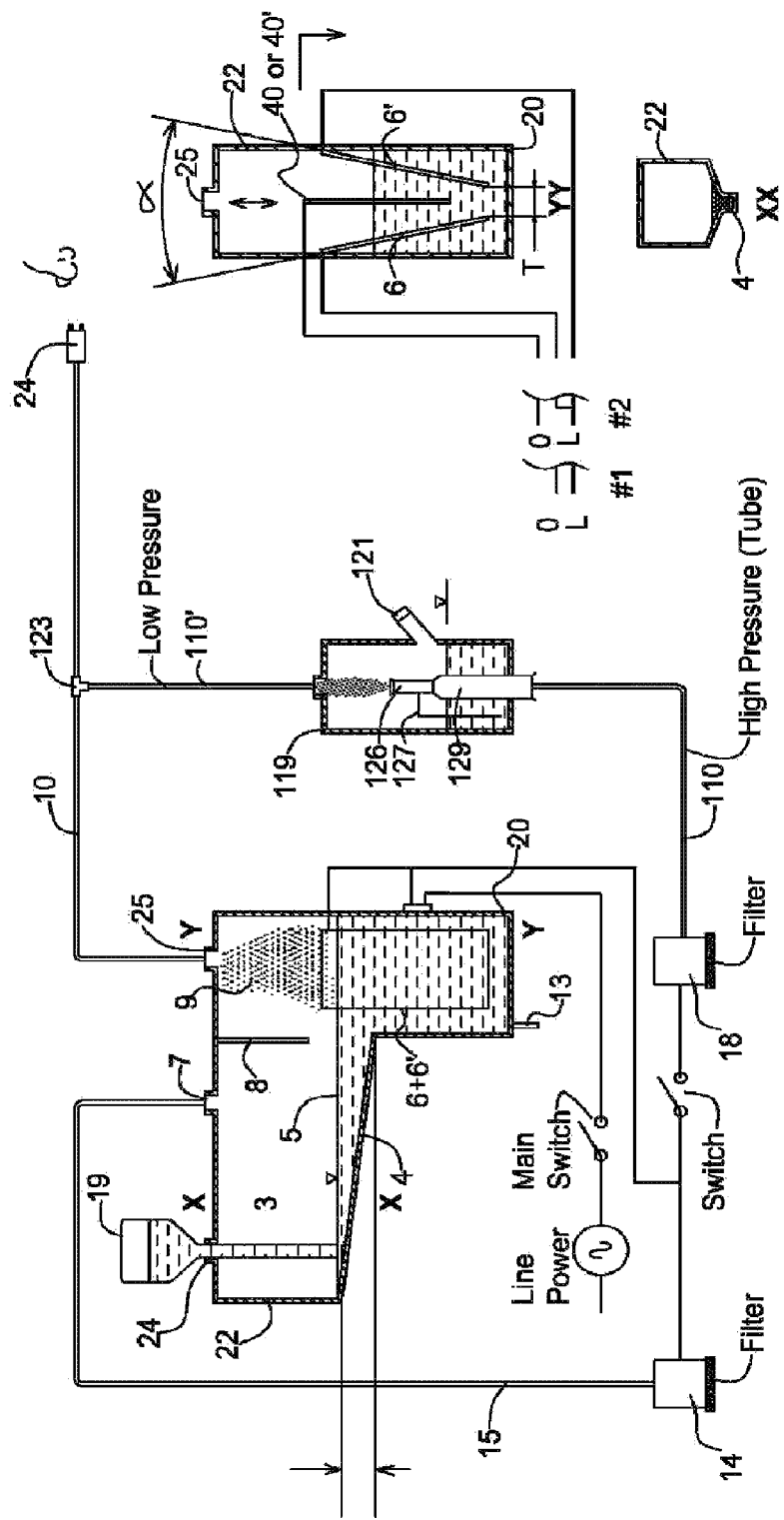
FIG. 2 illustrates three cross sections of device according to another embodiment of the invention.

FIG. 2 illustrates three cross sections of device 100 according to another embodiment of the invention. The first cross section is taken along an imaginary longitudinal axis. The other two cross sections were taken along two latitudinal axes X-X and Y-Y.

Device 100 differs from device 1 of FIG. 1 by including an additional compressor 18, an additional gas pipe 110, a mixing system 119, and an additional mixture inlet 123 that enables a provision of a mixture of gas and additional fluid droplets to the patient. Thus, device 100 can provide to a patient a mixture of gas, vapor and additional fluid droplets. Conveniently, the additional fluid is a drug or another type of fluid that should not be heated.

The additional compressor 18 is characterized by a higher capacity than compressor 14 and outputs gas at higher pressure than the pressure of gas that is outputted by compressor 14. Accordingly, the additional mixture that is outputted from the mixing system 119 Is mixed with the mixture that is output from housing 19 and exits pipe 10 via nozzle 24.

Mixing system 119 includes a fluid inlet and cap 121 as well as an inner short constricted Venturi tube 126 and a larger inlet 129 for receiving gas from additional gas pipe 110 and a much smaller tube 127 from which additional fluid is sucked and tiny droplets are ejected towards additional mixture pipe 110 that is connected to pipe 10. The additional fluid is maintained between the inner Venturi tubes 126, 129 and the inner walls of the mixing system 119.

FIG. 3 is a flow chart of a method 200 for providing a controlled mixture of gaseous medium and fluid, according to an embodiment of the invention. Method 200 starts by stage 210 of providing a device that includes multiple tilted heating elements, and a housing that includes a fluid reservoir inlet that is adapted to receive an inverted fluid reservoir, a gas inlet that is adapted to receive pressurized gas from a gas pipe, a gas-vapor outlet and a optionally a gas directing barrier that is positioned between the gas inlet and the gas-vapor outlet such as to direct gas to flow towards the gas-vapor outlet.

Conveniently, stage 220 can further include providing additional components that enable providing a mixture of gas and additional fluid droplets to a patient. For example, a device that includes such additional components is described in FIG. 2.

Stage 220 is followed by stage 240 of activating the device to provide a controller mixture of gaseous medium and fluid. During the activation fluid is provided, the fluid is heated, gas flows through the device and vapors are provided to patient. Optionally, additional mixture is also provided to the patient.

Method 200 can also include an optional stage 230 of setting the temperature of the mixture of gas and fluid by adjusting the device. This can include determining the height of the inverted fluid reservoir, determining the type of the fluid, determining the angle between the tilted heating elements and the like.

All the aforesaid has been described for the purpose of illustration only and is not intended to be limitative. Many variations in the various means and devices of the device of the invention may be provided, without exceeding the scope of the invention.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method comprising: providing a device that comprises multiple tilted heating elements, and a housing that comprises a fluid reservoir inlet that is adapted to receive an inverted fluid reservoir, a gas inlet that is adapted to receive pressurized gas from a gas pipe, and a gas-vapor outlet; and activating the device to provide a controlled mixture of gas and fluid.

2. The method according to claim 1 further comprising setting the temperature of the mixture of gas and fluid by adjusting the device.

3. The method according to claim 2 wherein adjusting comprises determining a height of the inverted fluid reservoir.

4. The method according to claim 2 wherein the comprises determining a type of the fluid.

5. The method according to claim 2 wherein adjusting comprises determining an angle between the tilted heating elements.

6. The method according to claim 1 further comprising providing a mixture of gas and additional fluid droplets to a patient.

7. A device comprising: multiple tilted heating elements, and a housing that comprises a fluid reservoir inlet that is adapted to receive an inverted fluid reservoir, a gas inlet that is adapted to receive pressurized gas from a gas pipe, and a gas-vapor outlet; wherein the multiple tilted heating elements are placed at least partially within fluid within the housing and are adapted to heat the fluid so as to generate vapors; and the device is adapted to output, via the gas-vapor outlet a mixture of gas and vapor.

8. The device according to claim 7 further comprising a gas directing barrier that is positioned between the gas inlet and the gas-vapor outlet so as to direct gas to flow towards the gas-vapor outlet.

9. The device according to claim 7 wherein a bottom of the housing comprises a sloped duct portion.

10. The device according to claim 7 further comprising an additional gas pipe, a mixing system, and an additional mixture inlet adapted to provide a mixture of gas and additional fluid droplets.

* * * * *